United States Patent [19]

Cohen et al.

[11] Patent Number: 5,412,121

[45] Date of Patent: May 2, 1995

[54] PROCESS FOR THE PREPARATION OF 4-HYDROXY-3[2H]FURANONES

[75] Inventors: A. M. Cohen, Amersfoort; W. Lenselink, Voorthuizen; C. van Ek, Hoogland, all of Netherlands

[73] Assignee: Tastemaker, Cincinnati, Ohio

[21] Appl. No.: 163,563

[22] Filed: Dec. 8, 1993

Related U.S. Application Data

[63] Continuation of Ser. No. 941,612, Sep. 8, 1992, abandoned.

[30] Foreign Application Priority Data

Sep. 10, 1991 [EP] European Pat. Off. ........... 91202315

[51] Int. Cl.$^6$ ............................................ C07D 307/60
[52] U.S. Cl. .................................................... 549/477
[58] Field of Search .......................................... 549/477

[56] References Cited

U.S. PATENT DOCUMENTS

| | | | |
|---|---|---|---|
| 3,455,702 | 7/1969 | Willhalm et al. | 549/477 |
| 3,651,097 | 3/1972 | van den Ouweland et al. | 549/477 |
| 4,127,592 | 11/1978 | Cohen | 549/477 |

OTHER PUBLICATIONS

House, H. O., "The alkylation of active methylene compounds", *Modern Synthetic Reactions,* 2nd Ed., Bejamin/Cummings Publ. Comp., London 1972, p. 518.

Hilgetag, G. et al, "COC linkage by replacement of halogen by Carbon", *PreparativeOrganic Chemistry,* 4th Ed., John Wiley & Sons, New York 1972 (pp. 912–913).

March, J., *Advanced Organic Chemistry,* 3rd Ed., John Wiley & Sons, New York 1985 (pp. 411–413).

*Primary Examiner*—Johann Richter
*Assistant Examiner*—John Peabody
*Attorney, Agent, or Firm*—Wood, Herron & Evans

[57] ABSTRACT

A process is provided for the preparation of 5-alkyl-4-hydroxy-3[2H]furanones and/or 2,5-dialkyl-4-hydroxy-3[2H]furanones, wherein each alkyl group independently has one to six carbons, comprising (a) saponifying an ester selected from the group of 3,4-dihydroxyfurans substituted at the 2- and/or 5-position with one or two carbalkoxy groups, wherein each alkoxy group independently contains one to six carbon atoms, and optionally substituted at the 2- or 5-position with an alkyl group with one to six carbon atoms, or tautomeric forms or keto-enol isomers thereof, (b) treating with one or two alkylation reagents which independently may have one to six carbon atoms, and (c) subsequently recovering the 5-alkyl-4-hydroxy-3[2H]furanones and/or 2,5-dialkyl-4-hydroxy-3[2H]furanones.

10 Claims, No Drawings

PROCESS FOR THE PREPARATION OF 4-HYDROXY-3[2H]FURANONES

This application is a continuation of application Ser. No. 941,612, filed Sep. 8, 1992, now abandoned.

BACKGROUND OF THE INVENTION

This invention relates to a process for the preparation of 5-alkyl-4-hydroxy-3[2H]furanones and 2,5-dialkyl-4-hydroxy-3[2H]furanones or tautomeric forms thereof, wherein the alkyl radicals independently may comprise one to six carbon atoms.

The furanones, subject of the present invention, are flavoring and perfume ingredients and have been widely utilized for the reconstitution of good quality flavors and fragrances. After their identification as volatile flavor component in nature, e.g., in pineapple (J. O. Rodin et al., J. Food Sci. 30, 280 (1965), 4-hydroxy-3[2H]furanones have found an ever increasing acceptance also based upon their versatility and applicability in a great variety of different flavor types. Their use in flavoring agents has been described in, for example, German patent application No. 1,915,788 for bakery products, Dutch patent applications No. 70 04 150 or meat flavors, German patent application No. 2,202,065 and No. 2,202,066 for tobacco flavoring, Swiss patent No. 540,650 for cooked fruit flavors and European patent application No. 0,167,214 as a sugar simulating compound. Their use as perfume ingredient is described in, for example, German patent application No. 2,509,668 and their use in insect attractant compositions is mentioned in U.S. Pat. No. 4,447,447.

For the preparation of 2,5-dialkyl-4-hydroxy-3[2H]furanones many synthetic routes have been suggested. However, all of these either are laborious non-economical laboratory methods with low overall yields, or use rare, expensive, dangerous and toxicologically undesirable methods and/or raw materials. Methods heretofore proposed for the preparation of 5-alkyl-4-hydroxy-3[2H]furanones and 2,5-dialkyl-4-hydroxy-3[2H]furanones have been described, for example, in the German patent applications No. 1,932,799, 2,163,223, 2,359,891, 2,812,713 and 2,845,843. Swiss patent No. 491,904, European patents No. 0,000,907 and 0,055,976 in Japanese patent application No. 79,115,369 and by L. Re et al., Helv. Chim. Acta 56, (6), 1882 (1973), M. Baumann et al., Synthesis 1981 (9) 709 and C. H. Wong et al., J. Org. Chem. 48 (20), 3493 (1983). These methods of preparation comprise cyclization of straight chain compounds of proper oxidation level, and oxidations of 3[2H] furanone derivatives. In German patent application 2,812,713 alkylation of sodium salts of 2-carbalkoxy-5-alkyl-3,4-dihydroxyfuran is set forth. This method requires large excesses of the alkylation agent, very long reaction periods at elevated temperatures, which is unfavorable for both purity and yield because of the general thermolability of 4-hydroxy-3[2H]furanones, water-free conditions, nitrogen atmosphere and complex systems of organic solvents. Yields are moderate to low. As an explicit condition for this method of preparation, it is claimed that the alkylation step of sodium salts of 2-carbalkoxy-5-alkyl-3,4-dihydroxyfuran is performed prior to the hydrolysis of the carbethoxy group of the resultant reaction product.

SUMMARY OF THE INVENTION

According to the present invention, it has been found unexpectedly that 5-alkyl-4-hydroxy-3[2H]furanones and 2,5-dialkyl-4-hydroxy-3[2H]furanones can be prepared in good yields in a technically very simple and commercially very attractive way using readily accessible, abundantly available basic chemicals. This process can easily be carried out in an aqueous medium.

The process of the present invention comprises (a) saponification of an ester selected from the group of 3,4-dihydroxyfurans substituted at the 2- and/or 5-position with one or two carbalkoxy groups, wherein the alkoxy groups independently contain one to six carbon atoms or tautomeric forms or keto-enol isomers thereof; (b) subsequent treatment of the hydrolysate with one or two alkylation reagents by which one or two alkyl group are introduced, which groups independently may contain one to six carbon atoms; (c) recovery of the 5-alkyl-4-hydroxy-3[2H]furanones and/or 2,5-dialkyl-4-hydroxy-3[2H]furanone. It should be understood that, because of the tautomeric nature of the subject compounds, when mentioning a 4-hydroxy-3[2H] furanone the tautomeric form is also included. The starting ester used in the saponification is optionally substituted at the 2 or 5 position with an alkyl group with one to six carbon atoms.

DETAILED DESCRIPTION OF THE INVENTION

The invention is based on the surprising and unexpected finding that it is possible to alkylate the carboxylic acid salt, with simultaneous decarboxylation. This finding has opened the route to various advantageous and easy preparation methods for the present product.

The alkyl groups in the 5-alkyl-4-hydroxy-3[2H]furanones and/or 2,5-dialkyl-4-hydroxy-3[2H]furanones are preferably selected from the group of alkenyl, alkynyl, cycloalkyl and cycloalkenyl groups of at most six carbon atoms. More particularly, the alkyl groups are independently selected from methyl, ethyl and n-hexyl groups.

The starting esters for the process of the present invention are easily prepared according to methods known to the art, e.g., according to the method of British patent No. 1,601,934. It should be understood, that according to the method, mixtures of different esters are obtained with respect to the alkyl moiety of the carbalkoxy group in case the starting materials and the alkaline condensing agent contain different alkoxy groups.

According to the present invention, such mixtures of different esters are equally suitable for the preparation of 5-alkyl-4-hydroxy-3[2H]furanones and/or 2,5-dialkyl-4-hydroxy-3[2H]furanones as the single esters.

Suitable furanones prepared in accordance with the present invention are 4-hydroxy-3[2H]furanones selected from the group 2-methyl-4-hydroxy-3[2H] furanone, 5-methyl-4-hydroxy-3[2H] furanone, 2,5-dimethyl-4-hydroxy-3[2H] furnone, 2-ethyl-4-hydroxy-3[2H] furanone, 5-ethyl-4-hydroxy-3[2H] furanone, 2-methyl-5-ethyl-4-hydroxy-3[2H] furanone and 2-ethyl-5-methyl-4-hydroxy-3[2H] furanone, prepared according to the process of claim 1 or claim 4.

The hydrolysis of the starting esters of the process of the invention can be performed according to the methods known to the art for effecting hydrolysis of esters in general. For economical and practical reasons the hydrolysis preferably is carried out in an aqueous medium by the use of an alkali metal hydroxide, such as lithium hydroxide, sodium hydroxide and potassium hydroxide. The temperature of the hydrolysis step and the amounts of base and solvent used are not critical. Suitable temperatures range from 0° to 100° C., practicably advantageously, temperatures around room temperature are practiced. The preferred solvent is water.

Because of the acidic nature of the hydroxyl moieties in the starting esters the amount of base, such as sodium hydroxide or potassium hydroxide employed, should compensate for the neutralization effect in order to create a basicity high enough to effect the hydrolysis under alkaline conditions. Preferably the amount of base used ranges from 3 to 7 molar equivalents of the amount of starting esters.

The alkylation reagents effective in the process of the present invention can be chosen from the wide variety of reagents known as alkylation agents to the art suitable to introduce alkyl moieties from one to six carbon atoms, e.g., alkyl halides, alkyl sulphates, alkyl arylsulphates, alkyl carbonates and the like, whether or not in conjunction with activators like iodine, iodides and the like. The alkyl moiety has preferably one to six carbon atoms. Most preferred are alkyl chlorides, alkyl bromides and alkyl sulfates. Suitable temperatures for the alkylation range from 0° to 100° C., whereby the preferred temperatures are around room temperature, i.e., from about 15° to about 30° C.

According to the present invention, the starting esters may also be processed as intermediate reaction products without prior isolation, e.g., from the process set forth in German patent 2,812,713 describing the condensation of dialkyl alpha-alkyldiglycolic esters with dialkyl oxalates.

Accordingly, a preferred embodiment of the invention comprises a process for the preparation of 5-alkyl-4-hydroxy-3[2H]furanones and/or 2,5-dialkyl-4-hydroxy-2[2H] furanones, wherein each alkyl group independently has one to six carbon atoms, comprising:

(a) condensing a dialkyl diglycolate or a dialkyl 2-alkyl-glycolate, wherein each alkyl group independently has one to six carbon atoms, with a dialkyl oxalate, wherein each alkyl group independently contains one to six carbon atoms in the presence of an alkaline condensing agent;

(b) subsequent saponification of at least one of the carbalkoxy moieties of the resulting product;

(c) subsequent treatment with one or two alkylation reagents which independently have one to six carbon atoms;

(d) subsequent recovery of the 5-alkyl-4-hydroxy-3[2H]furanones and/or 2,5-dialkyl-4-hydroxy-3[2H]furanones.

The following examples illustrate the invention.

EXAMPLE 1

A solution of 48 g of sodium hydroxide and 37.2 g of ethyl 5-methyl-3,4-dihydroxy-2-furoate of 98.4% purity in 225 ml of water was allowed to stand at room temperature for 40 hours. The mixture was diluted with 200 g of water and 22.8 g of gaseous methyl bromide was added with stirring over a period of one hour at room temperature followed by an additional stirring period of two hours. The pH of the solution was adjusted to 5 by the addition of concentrated hydrochloric acid solution. Extraction with methyl t-butyl ether yielded 21.5 9 of 2,5-dimethyl-4-hydroxy-3[2H] furanone of 95.3% purity (molar yield 81.4%).

EXAMPLE 2

A solution of 32 g of sodium hydroxide and 33 g of a mixture containing 37.1% of methyl 5-methyl-3,4-dihydroxy-2-furoate and 52.1% of ethyl 5-methyl-3,4-dihydroxy-2-furoate in 320 ml of water was allowed to stand at room temperature for 20 hours. To the resulting mixture is added at 0° C. in one hour 25.2 g of dimethyl sulphate followed by an additional stirring period of three hours at 0° C. The pH of the solution was adjusted to 6.5 by the addition of concentrated hydrochloric acid solution. Extraction with methyl t-butyl ether yielded 18.1 g of 2,5-dimethyl-4-hydroxy-3[2H] furanone of 88.8% purity (molar yield 76.6%).

EXAMPLE 3

To a suspension of 113.4 g of sodium methylate in 750 g of methyl t-butyl ether was added at 5° C. in one hour 146 g of diethyl oxalate followed by a stirring period of one hour at 5° C. Then 204 g of diethyl 2-methyldiglycolate in two hours was added at 5° C. and the mixture was stirred for four hours at that temperature followed by a reflux period of three hours. The reaction mixture was added to 797 g of 8.9% hydrochloric acid solution at 20° C. and the pH of the resulting mixture was adjusted to 5 with 33% sodium hydroxide solution. To the separated upper layer was added with stirring 903 g of 17.8% sodium hydroxide solution at 20° C. The layers were allowed to settle and the separated lower layer was kept at 20° C. for 20 hours. Then, 200 g of water was added, 104 g of methyl bromide was introduced at 20° C. in one hour, and the mixture was stirred for another hour; and the pH of the solution was adjusted to 6.5 by the addition of concentrated hydrochloric acid solution. Extraction with methyl t-butyl ether yielded 95 g of 2,5-dimethyl-4-hydroxy-3[2H] furanone of 97.3% purity (molar overall yield 72.2%).

EXAMPLE 4

A solution of 20 g of sodium hydroxide and 24.4 g of diethyl 3,4-dihydroxy-2,5-difuroate in 180 ml of water was allowed to stand at room temperature for 45 hours. Then, 48 g of methyl bromide was introduced in 5 hours at room temperature. The pH of the solution was adjusted to 5 by the addition of concentrated hydrochloric acid solution. Extraction with methyl t-butyl ether yield 9 g of 2,5-dimethyl-4-hydroxy-3[2H] furanone of 86.6% purity (molar yield 60.9%).

EXAMPLE 5

A solution of 108 g of sodium hydroxide and 116 g of methyl 5-methyl-3,4-dihydroxy-2-furoate of 94% purity in 935 ml of water was allowed to stand at room temperature for 20 hours. Then 88 g of ethyl bromide was added in one hour at room temperature followed by an additional stirring period of four hours. The pH of the solution was adjusted to 6 by the addition of concentrated hydrochloric acid solution. Extraction with methyl t-butyl ether and flash-distillation yielded 82 g of an isomeric mixture of 2-ethyl-5-methyl-4-hydroxy-3[2H] furanone and 2-methyl-5-ethyl-4-hydroxy-3[2H] furanone of 92.2% purity (molar yield 84.0%), b.p. 95°–100° C. at 0.3 mm Hg.

EXAMPLE 6

A solution of 48 g of sodium hydroxide and 37.2 g of ethyl 5-methyl-3,4-dihydroxy-2-furoate of 95.3% purity in 225 ml of water was allowed to stand at room temperature for 40 hours. Then, 34 g of ethyl iodide was added in one hour at room temperature followed by an additional stirring period of six hours. The pH of the solution was adjusted to 6 by the addition of concentrated hydrochloric acid solution. Extraction with methyl t-butyl ether and flash-distillation yield 22.9 g of an isomeric mixture of 2-ethyl-5-methyl-4-hydroxy-3[2H] furanone and 2-methyl-5-ethyl-4-hydroxy-3[2H] furanone of 92.6% purity (molar yield 78.3%).

EXAMPLE 7

Example 3 was repeated at a four times larger scale and substituting methyl bromide with an equimolar amount of ethyl bromide yielding 367 g of an isomeric mixture of 2-ethyl-5-methyl-4-hydroxy-3[2H] furanone and 2-methyl-5-ethyl-4-hydroxy-3[2H] furanone of 96.3% purity (molar overall yield 62.2%).

EXAMPLE 8

A solution of 32 g of sodium hydroxide and 34.4 g of methyl 5-methyl-3,4-dihydroxy-2-furoate of 99.8% purity in 235 ml of water was allowed to stand at room temperature for 20 hours. Then, 49.2 g. of n-propyl bromide was added at room temperature followed by an additional stirring period of 20 hours. The pH of the solution was adjusted to 6 by the addition of concentrated hydrochloric acid solution. Extraction with methyl t-butyl ether yielded 25.3 g of an isomeric mixture of 2-n-propyl-5-methyl-4-hydroxy-3[2H] furanone and 2-methyl-5-n-propyl-4-hydroxy-3[2H]furanone of 81.8% purity (molar yield 66.5%), b.p. 95°–100° C. at 0.2 mm Hg.

EXAMPLE 9

Example 6 was repeated substituting ethyl iodide with 49.2 g of i-propyl bromide yielding 17 g of an isomeric mixture of 2-i-propyl-5-methyl-4-hydroxy-3[2H] furanone and 2-methyl-5-i-propyl-4-hydroxy-3[2H] furanone of 93.2% purity (molar yield 53.3%), b.p. 78°–83° C. at 0.2 mm Hg.

EXAMPLE 10

Example 1 was repeated at half the scale substituting methyl bromide with 29.8 g of cyclopentyl bromide yielding 9.3 g of an isomeric mixture of 2-cyclopentyl-5-methyl-4-hydroxy-3[2H] furanone and 2-methyl-5-cyclopentyl-4-hydroxy-3[2H] furanone of 92.5% purity (molar yield 48.1%), b.p. 120°–125° C. at 0.2 mm Hg.

We claim:

1. A process for the preparation of 5-alkyl-4-hydroxy-3[2H] furanones and/or 2,5-dialkyl-4-hydroxy-3[2H] furanones, wherein each alkyl group of said alkyl or dialkyl independently has one to six carbons comprising
    (a) saponifying an ester selected from the group of 3,4-dihydroxyfurans substituted at the 2-and/or 5-position with one or two carbalkoxy groups, wherein each alkoxy group independently contains one to six carbons, and optionally substituted at the 2-or 5-position with an alkyl group with one to six carbon atoms, or tautomeric forms or keto-enol isomers thereof to produce a hydrolyzate,
    (b) treating the hydrolyzate with one or two alkylation reagents which independently may have one to six carbons to simultaneously alkylate and decarboxylate at the 2- and/or 5-position, and
    (c) recovering the 5-alkyl-4-hydroxy-3[2H] furanones and/or 2, 5-dialkyl-4-hydroxy-3[2H] furanones.

2. The process according to claim 1 wherein at least one of the alkyl groups is selected from the group of alkenyl, alkynyl, cycloalkyl and cycloalkenyl groups of at most six carbons.

3. The process according to claim 1 wherein the alkyl groups independently are selected from methyl, ethyl and n-hexyl groups.

4. A process for the preparation of 5-alkyl-4-hydroxy-3[2H] furanones and/or 2, 5-dialkyl-4-hydroxy-3-3[2H] furanones, wherein each alkyl group of said alkyl or dialkyl independently has one to six carbons comprising
    (a) condensing a dialkyl diglycolate or a dialkyl 2-alkyl-glycolate, wherein each alkyl group of said alkyl or dialkyl independently has one to six carbons, with a dialkyl oxalate, wherein each alkyl group of said dialkyl independently contains one to six carbons, in the presence of an alkaline condensing agent,
    (b) saponifying at least one of the carbalkoxy moieties of the resulting product,
    (c) treating (b) with one or two alkylation reagents which independently have one to six carbons to simultaneously alkylate and decarboxylate at the 2- and/or 5-position, and
    (d) recovering the 5-alkyl-4-hydroxy-3[2H] furanones and/or 2, 5-dialkyl-4-hydroxy-3[2H] furanones.

5. The process according to claim 4 wherein at least one of the alkyl groups is selected from the group of alkenyl, alkynyl, cycloalkyl and cycloalkenyl groups of at most six carbons.

6. The process according to claim 4 wherein the alkyl groups independently are selected from methyl, ethyl and n-hexyl groups.

7. The process of claim 1 conducted in an aqueous medium.

8. The process of claim 4 conducted in an aqueous medium.

9. The method of claim 7 wherein said medium contains base from about 3 to about 7 molar equivalents of the amount of the starting esters.

10. The method of claim 8· wherein said medium contains base from about 3 to about 7 molar equivalents of the amount of the starting esters.

* * * * *